United States Patent [19]

Niewisch

[11] Patent Number: 5,088,501
[45] Date of Patent: Feb. 18, 1992

[54] MEASUREMENT ARRANGEMENT FOR ACQUIRING A SIGNAL CORRESPONDING TO RESPIRATORY MOTION

[75] Inventor: Joachim Niewisch, Nuremberg, Fed. Rep. of Germany

[73] Assignee: Siemens Aktiengesellschaft, Berlin and Munich, Fed. Rep. of Germany

[21] Appl. No.: 599,016

[22] Filed: Oct. 17, 1990

[30] Foreign Application Priority Data

Oct. 20, 1989 [DE] Fed. Rep. of Germany ....... 3935083

[51] Int. Cl.$^5$ .............................................. A61B 5/08
[52] U.S. Cl. .................................... 128/721; 128/782
[58] Field of Search ............... 128/721, 722, 664–666, 128/671, 782

[56] References Cited

U.S. PATENT DOCUMENTS

| | | |
|---|---|---|
| 2,194,809 | 5/1939 | Powell, Jr. . |
| 4,324,259 | 4/1982 | Wright . |
| 4,602,643 | 7/1986 | Dietz .................................... 128/721 |
| 4,664,129 | 5/1987 | Helzel et al. . |
| 4,813,428 | 3/1989 | Muraki et al. ....................... 128/721 |
| 4,945,916 | 8/1990 | Kretschmer et al. ................ 128/671 |
| 4,989,612 | 2/1991 | Fore .................................... 128/721 |

FOREIGN PATENT DOCUMENTS

2559051 8/1985 France .................... 128/666

OTHER PUBLICATIONS

"Optical Multimode Fiber Sensors: A Review", Spenner et al., Laser und Optoelektronik, Vol. 3 1983 pp. 226–234.

"Fiber-Optic Diaphragm-Curvature Pressure Transducer" Lawson et al., Optics Letters, Vol, 8, No, 5, May, 1983, pp. 286–288.

*Primary Examiner*—Lee S. Cohen
*Attorney, Agent, or Firm*—Hill, Van Santen, Steadman & Simpson

[57] ABSTRACT

An arrangement for acquiring a signal corresponding to respiratory motion includes a pneumatic respiratory belt which generates a mechanical pressure signal and a pressure transducer which converts the incoming mechanical pressure signal into an optical signal using a flexible membrane, which is deformed by the pressure signal, and which has a reflective surface thereon so that a modulated light signal is generated corresponding to the pressure signal. The transducer can be constructed avoiding metallic materials, thereby permitting the transducer to be disposed in the radio frequency field of a magnetic resonance imaging tomography apparatus, and thus in the immediate proximity of the respiratory belt. The pressure signals from the belt, since they must travel only a relatively short distance to the transducer, do not significantly deteriorate and thus the sensitivity of the measuring arrangement is increased.

9 Claims, 1 Drawing Sheet

MEASUREMENT ARRANGEMENT FOR ACQUIRING A SIGNAL CORRESPONDING TO RESPIRATORY MOTION

BACKGROUND OF THE INVENTION

1. Field of the Invention

The present invention is directed to a measuring arrangement for acquiring a signal corresponding to the respiratory motion of a patient, and in particular to such an arrangement wherein a pneumatic pressure signal is obtained corresponding to the respiratory motion which is converted into an intensity-modulated optical signal.

2. Description of the Prior Art

It is known when obtaining a tomogram using magnetic resonance imaging (MRI or NMR) techniques to monitor the respiratory motion of the examination subject during certain types of exposures, so that the generation of the image can be gated, synchronized with the respiratory motion, to avoid motion artifacts in the image. For this purpose, it is known to obtain a pressure signal corresponding to the motion caused by respiration using a pneumatic respiratory belt. The pneumatic pressure signal is then conducted via a pressure conduit to a location remote from the belt, wherein the signal is converted into an electrical signal by a capacitive transducer or by a piezoelectric pressure sensor.

A measurement apparatus of this type is described in U.S. Pat. No. 4,324,259, wherein the pressure signal is supplied to a capacitive transducer wherein one of the capacitor plates is mounted on a flexible membrane which is deformed by the pressure signal. This causes the spacing between the plates to vary, thereby resulting in a capacitance signal which is modulated by the pressure signal. If this type of device were to be used in the environment of a magnetic resonance imaging tomography apparatus, the transducer portion of the device would necessarily have to placed at a considerable distance from the examination subject wearing the respiratory belt, the subject being disposed in the magnetic resonance imaging apparatus. This is because, due to the influences of the strong high frequency fields on electronic components, it is necessary to place all electrically conductive materials at a location sufficiently remote from the fields so that the components are not affected by the fields. The necessity of using such a long pressure conduit between the belt and the transducer unavoidably results in deterioration of the pressure signal due to the inactive volume of the conduit. This decreases the sensitivity of the measuring arrangement, and may result in a faulty correlation between the derived electrical signal and the actual respiratory motion.

A respiratory motion sensor specifically designed for use in a magnetic resonance imaging environment is disclosed in U.S. Pat. No. 4,664,129. This known arrangement includes a belt having a buckle consisting of two mating parts which are mechanically connected so as to be relatively movable. In one embodiment, a light transmitter is disposed in one of the parts, and a light receiver is disposed in the other part. A light polarizer is disposed in front of the light receiver, so that movement due to respiration will cause the light from the transmitter to be polarized by different amounts, since the light will arrive at different directions due to the motion. By analyzing the degree of polarization, a signal corresponding to movement of the examination subject is obtained. In another embodiment of the invention, the transmitter and receiver are disposed in the same belt part, and the other part contains a mirror which reflects the light from the transmitter back to the receiver. A mechanical, pneumatic signal is thus not used at all in this arrangement.

SUMMARY OF THE INVENTION

It is an object of the present invention to provide an arrangement for acquiring a signal corresponding to respiratory motion which can be used in the environment of a magnetic resonance imaging tomography apparatus which makes use of a pneumatic pressure signal without significant degradation of the pressure signal.

In particular, it is an object of the present invention to provide such a measuring arrangement wherein the pressure transducer can be located within the high frequency field without being disturbed thereby.

The above objects are achieved in a measuring arrangement which includes a pneumatic respiratory belt adapted to be worn by an examination subject, the belt generating a pneumatic pressure signal which is conducted via a relatively short pressure conduit to a pressure transducer. The pressure transducer has a flexible membrane therein which is deformed by the pressure signal. The membrane has a reflective surface, on which light from a light source is incident, which is displaced by the pneumatic signal and thereby generates an intensity-modulated optical signal. The optical signal can be forwarded without disturbance or loss over long distance via optical fibers, and is uninfluenced by the radio frequency fields of the nuclear magnetic resonance tomography apparatus.

DESCRIPTION OF THE PREFERRED EMBODIMENTS

Figure 1:
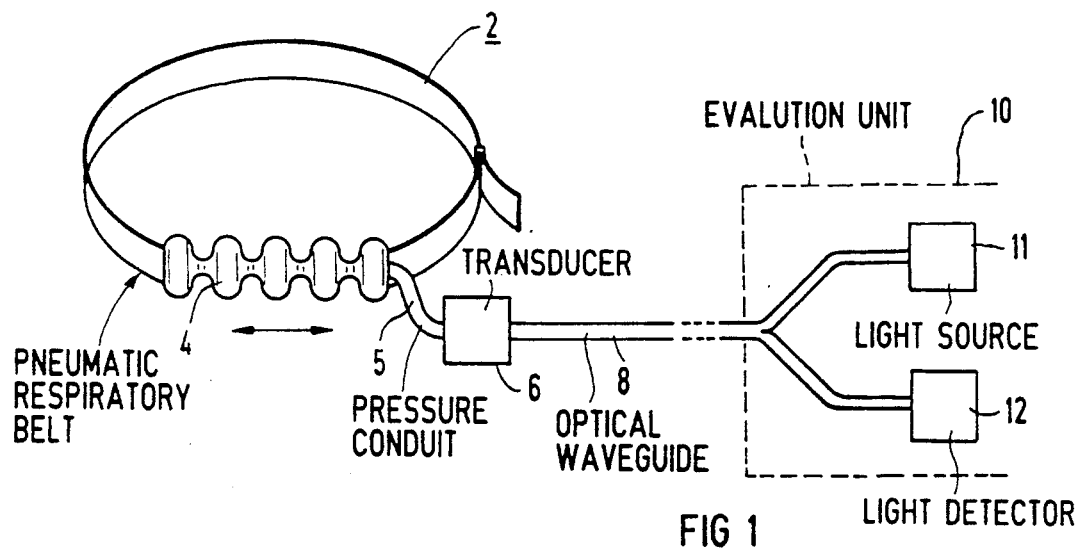
FIG. 1 is a schematic drawing of a respiratory measurement arrangement constructed in accordance with the principles of the present invention.

As shown in FIG. 1, a measuring arrangement for acquiring a respiratory motion signal constructed in accordance with the principles of the present invention includes a pneumatic respiratory belt 2 of known construction having a movable portion 4 which is displaced by the respiratory motion of a person wearing the belt 2. The movable portion 4 may be in the form of a bellows, for example, or of any other suitable structure for generating a pneumatic signal. The pneumatic signal, generated by pressure changes as a result of the respiratory motion of the subject, is conducted via a conduit 5 to a pressure transducer 6, which converts the pressure changes into an optical signal. The optical signal is forwarded via a light wave guide to a light receiver 12, for example, a photodiode, in an evaluation unit 10. The transducer 6 is also connected via the light wave guide 8 to a light source 11, for example an LED, also disposed in the evaluation unit 10. The light source 11 supplies the light which will be modulated in the transducer 6 in the manner described below, with the modulated light being supplied via the light wave guide 8 to the light receiver 12.

The output of the light receiver 12 is supplied to processing circuitry (not shown) which analyzes the electrical signal, corresponding to the modulated optical signal, using any number of known techniques.

The light supplied by the light source 11, and forwarded via the light wave guide 8 to the transducer 6, is modulated by the pressure signal supplied from the conduit 5 to the transducer 6, and is conducted back to the light receiver 12 via the light wave guide 8. The modulation, for example, may be a modification of the spectral composition of the light, or a modification of the light intensity. A transducer which generates an intensity modulated optical signal is preferable, as disclosed, for example, in "Optical Multimode Fiber Sensors: A Review," Spenner et al., Laser Und Optoelektronik, Vol. 3, 1983, pp. 226–234, particularly FIGS. 12 and 13. The pressure transducer disclosed therein operates according to the principle of a fiber-optical reflection sensor for measuring distance changes. Such an optical sensor can be constructed without using magnetic or electrically conductive materials, so that unimpeded operation of the sensor can take place in the radio frequency field of a nuclear magnetic resonance tomography apparatus. The transducer can thus be disposed in the immediate proximity of the respiratory belt 2, so that the connecting conduit 5 can be either entirely eliminated, or will be extremely short.

Figure 2:
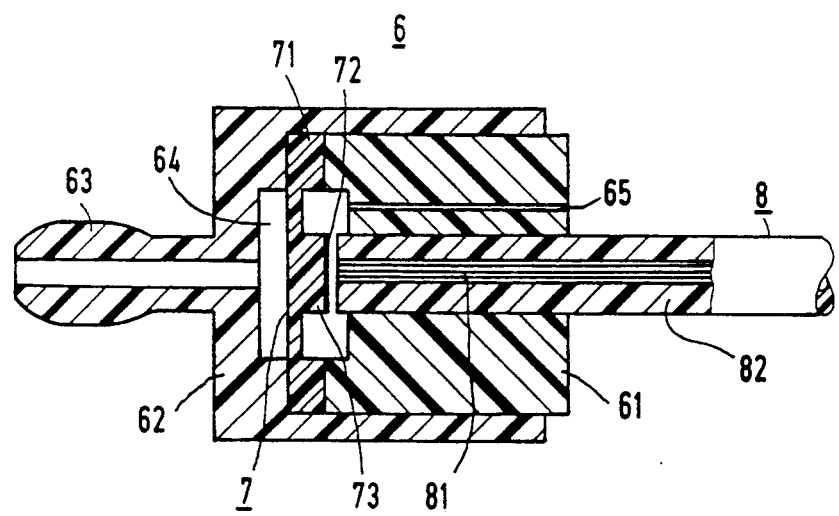
FIG. 2 is a side sectional view of the pressure transducer used in the arrangement of FIG. 1 constructed in accordance with the principles of the present invention.

A pressure transducer 6 which is especially suited for picking-up the pressure signal generated by the respiratory belt 2 is shown in FIG. 2. The transducer 6 contains a membrane 7 having a reinforced edge region 71 clamped between two housing parts 61 and 62 consisting of plastic, for example, polyvinylchloride (PVC). The housing part 62 is in the form of a hollow cylinder which is closed at one end by the insertion of the other housing part 61 therein. The housing part 62 also has a connector 63 for receiving the conduit 5.

The housing part 61 is also in the form of a hollow cylinder, with the central opening of the housing part 61 receiving the light wave guide 8.

The housing parts 61 and 62 are provided with respective recesses, which are arranged in registry with each other when the parts 61 and 62 are plugged together, the recesses forming an interior volume 64 in which the membrane 7 is disposed. The membrane 7 is clamped at its edge region 71 by the shoulders which limit the recesses. The interior volume 64 is divided into two chambers by the membrane 7. One of the chambers is in fluid communication with the belt 2 via the conduit 5, and the other is connected to the atmosphere via a vent 65 in the housing part 61. The housing parts 61 and 62 are preferably shaped so that the motion which can be undertaken by the membrane 7 is limited, as a protection against rupture of the membrane. Such rupture protection prevents destruction of the membrane given high pressure differences. Such high pressure differences may arise, for example, if the respiratory belt 2 were placed on the examination subject when the conduit 5 is already plugged to the transducer 6. If a pressure much lower than atmospheric pressure is present in the respiratory belt 2, the membrane 7 will close the opening in the connector 63, providing further protection against higher pressure differentials.

In a central region thereof, the membrane 7 has a rotationally symmetrical, for example circular, disc-shaped thickened portion 73 having a planar region which faces toward the end face of the light wave guide 8. The planar surface of the portion 73 is covered by a reflector 72. The surface of the membrane on which the reflector 72 is disposed and the end face of the light wave guide 8 are parallel to each other in the non-deflected condition of the membrane 7. In the exemplary embodiment of FIG. 2, the thickened portion 73 is in the form of a step on an annular, thin membrane, and the reflector 72 is disposed on the elevated flat side of the step. The thickened portion 73, however, may be disposed on the side of the membrane facing away from the light wave guide, or may be provided on both sides of the membrane 7. The thickened portion 73 is provided so that the ring-shaped annular zone surrounding the thickened portion 73 will be displaced by the pneumatic signal, but the reflective surface 72, when deflected with the annular zone, will remain substantially parallel to the end face of the wave guide 8.

The reflector 72 may be formed by an aluminum coated Mylar ® film or by a thin metallic layer directly vapor-deposited onto the membrane 7. Since either type of structure involves a metallic layer having a thickness only in the range of a few micrometers, the heating caused by the radio frequency field can be neglected. Preferably, however, the reflector 72 is a dielectric mirror.

The membrane 7 may consist, for example, of silicone rubber and is shaped by a vulcanization process at high temperature and high pressure.

In a preferred embodiment, an optical fiber bundle 81 is provided as the light wave guide, consisting, for example, of 50 μm fibers and having an overall diameter of 1.6 mm, and being surrounded by a cladding 82 consisting of polyvinylchloride (PVC). Separation of the fiber bundle 81 into a transmission skein and a reception skein can be undertaken arbitrarily, so that a statistical distribution of the transmission and reception fibers will be present at the end face of the fiber bundle located at the transducer 6. For reasons of reproducibility, a uniform distribution wherein every transmission fiber has a neighboring reception fiber is preferred.

Although modifications and changes may be suggested by those skilled in the art, it is the intention of the inventor to embody within the patent warranted hereon all changes and modifications as reasonably and properly come within the scope of his contribution to the art.

I claim as my invention:

1. A measuring arrangement for acquiring a signal corresponding to respiratory motion comprising:

a pneumatic respiratory belt adapted to be worn by an examination subject which generates a pneumatic pressure signal in response to respiratory motion;

a light source;

a pressure transducer in fluid communication with said belt via a releasable connection, permitting said belt to assume an arbitrary operating point before connection to said pressure transducer, for receiving said pneumatic pressure signal therefrom and in optical communication with said light source for receiving light therefrom, said pressure transducer having a flexible membrane deformable by said pneumatic pressure signal, said membrane carrying a reflector thereon disposed in the path of light from said light source and which generates an intensity-modulated optical signal corresponding to the deformations; and means for detecting said intensity-modulated optical signal.

2. A measuring arrangement as claimed in claim 1 wherein said means for detecting and said light source are in optical communication with said transducer via a common optical waveguide having an end face disposed in said transducer, and wherein said membrane has a planar surface on which said reflector is disposed facing said end face of said light waveguide.

3. A measuring arrangement as claimed in claim 1 wherein said membrane consists of silicone rubber.

4. A measuring arrangement as claimed in claim 1 wherein said reflector consists of an aluminum coated Mylar ® foil.

5. A measuring arrangement as claimed in claim 1 wherein said reflector is formed by a vapor-deposited metallic layer on said membrane.

6. A measuring arrangement as claimed in claim 1 wherein said reflector is a dielectric mirror.

7. A measuring arrangement as claimed in claim 2 wherein said membrane has a thickened region in registry with said end face of said light waveguide and wherein said reflector is disposed on said thickened region.

8. A measuring arrangement for acquiring a signal corresponding to respiratory motion comprising:

a pneumatic respiratory belt adapted to be worn by an examination subject and generating a pneumatic pressure signal corresponding to respiratory motion;

a light source;

transducer means containing no magnetic or electrically conductive parts in fluid communication with said belt via a releasable connection, permitting said belt to assume an arbitrary operating point before connection to said pressure transducer, for receiving said pneumatic signal therefrom and in optical communication with said light source for receiving light therefrom for converting said pressure signal into an intensity-modulated optical signal; and means for detecting said intensity-modulated optical signal.

9. A method for acquiring a signal corresponding to respiratory motion comprising the steps of:

attaching a pneumatic respiratory belt to an examination subject so that a pneumatic chamber in said belt, having a conduit in fluid communication therewith, generates a pressure signal in response to deformation of said chamber by respiratory motion;

maintaining said conduit open to the atmosphere during attachment of said belt to said examination subject so that said pressure chamber can assume an arbitrary deformation and thereby set an arbitrary operating point for said respiratory belt;

attaching said conduit, after attachment of said belt to said examination subject, to a pressure transducer via a releasable connection so that said pressure transducer is in fluid communication with said deformable chamber for receiving said pressure signal therefrom;

deforming a flexible membrane in said pressure transducer by said pressure signal, said flexible membrane having an optical reflector thereon;

directing a light source at said reflector on said flexible membrane for intensity-modulating light from said light source by movement of said reflector caused by deformation of said flexible membrane due to said pressure signal; and detecting light from said light source which has been intensity-modulated by deformation of said flexible membrane and using the intensity-modulated light as an indicator for respiratory motion.

* * * * *